United States Patent [19]

Cremonesi

[11] 4,338,401

[45] Jul. 6, 1982

[54] IMMOBILIZATION OF ENZYMES

[75] Inventor: Pietro Cremonesi, Milan, Italy

[73] Assignee: Italfarmaco S.p.A., Milan, Italy

[21] Appl. No.: 175,349

[22] Filed: Aug. 4, 1980

[30] Foreign Application Priority Data

Feb. 28, 1980 [IT] Italy .............................. 20213 A/80

[51] Int. Cl.³ ...................... C12N 11/10; C12N 11/04; C12N 11/08
[52] U.S. Cl. .................................. 435/178; 435/180; 435/182
[58] Field of Search ............... 435/174, 177, 178, 179, 435/180, 182, 176

[56] References Cited

U.S. PATENT DOCUMENTS

| | | | |
|---|---|---|---|
| 3,860,490 | 1/1975 | Guttag | 435/182 |
| 3,925,157 | 12/1975 | Hamsher | 435/180 |
| 3,957,580 | 5/1976 | Nelson | 435/181 X |
| 3,985,616 | 10/1976 | Weaver et al. | 435/182 X |
| 4,177,107 | 12/1979 | Kumakura et al. | 435/176 |
| 4,194,066 | 3/1980 | Kaetsu et al. | 435/182 |
| 4,195,129 | 3/1980 | Fukui et al. | 435/182 |
| 4,226,938 | 10/1980 | Yoshida et al. | 435/178 |
| 4,272,617 | 6/1981 | Kaetsu et al. | 435/182 |

*Primary Examiner*—David M. Naff
*Attorney, Agent, or Firm*—Bucknam and Archer

[57] ABSTRACT

Enzyme immobilization is carried out be adding to a suspension of polysaccharide in aqueous medium, a vinyl monomer and an enzyme, then a catalyst comprising a metallic salt, and irradiating the resulting mixture with ultraviolet light to cause polymerization and form a copolymer of the polysaccharide having enzymatic activity. The metallic salt is preferably a ferric salt and the vinyl monomer is preferably methylacrylate, glycidylmethacrylate, acrylonitride, bis-acyloylpiperazine or symmetrical N, N', N''-trisacryloyl-hexahydrotriazine.

14 Claims, No Drawings

IMMOBILIZATION OF ENZYMES

This invention relates to enzymes and more specifically to methods for immobilizing enzymes on a solid matrix. Many methods have been proposed for immobilizing enzymes on solid matrices and research is continuously being carried out to develop novel methods which will permit to immobilize enzymes on solid matrices by simpler techniques.

One object of the invention is to obtain the solid matrices with the enzymes immobilized in them in a technologically "viable form". Another object is to utilize as catalysts both in the synthesis as well as in the chemical or biological analysis, substances which exhibit the specific activity of the natural enzymes which are used in the immobilization reactions.

Several reaction schemes for the immobilization have been used. For instance, adsorption on a solid matrix has been extensively utilized. Other people have proposed the formation of a covalent bond between the macromolecule of the enzyme and a solid support which is either suitably activated or which contains suitable reactive groups. It has also been proposed to englobe the enzymes within a suitable support such as polymer gels, membranes on a protein base or synthetic polymers. Finally, the polymerization of suitable monomers in the presence of enzymes or the copolymerization of a suitable monomer with particularly activated enzymes has also been proposed. The latter two methods offer some advantages with respect to the former methods because the solid matrix on which the enzyme is supported may be suitably prepared for the specific requested use and when the appropriate physico-chemical characteristics as well as mechanical stability, porosity, hydrophobicity and hydrophily. Immobilization methods which utilize polymerization reactions have been reported for instance by J. J. Hamsher, French Pat. No. 7,325,614. These methods, however, are based upon a pre-reaction between a vinyl monomer which contains a reactive group and an enzyme with formation of an enzyme which carries vinyl groups followed by a reaction of copolymerization initiated by catalysts which are not specific initiators of immobilization reactions.

In other cases, there are utilized polymerization reactions in the presence of enzymes but the immobilization of the enzymes is obtained with functional reagents which bring about cross-linkages between the enzymes and the polymers such as cyanogen bromide, chlorotriazine, carbodiimide with polymers having a polyhydroxyethyl acrylate base or a base of polyacrylic acid, etc.

The term "copolymerization of proteins" designates methods which are analogous to the method discussed hereinabove and which have been discussed by D. Jaworek, H. Botsch, and J. Maier, Methods in Enzymology, 44, Ed. Klaus Mosbach, Academic Press; New York, 1976 p. 195-201, D. Jaworek, German Offenlegungsschrift, No. 22.60.185 and 21.28.743.

These methods are based upon the reaction of vinylation of enzymes with bifunctional monomers, for instance, acylating and/or alkylating agents, such as, 3,4-epoxybutene, 2,3-epoxypropylacrylate, and acryloyl chloride.

With this procedure, it is possible to immobilize several vinyl enzymes utilizing principally a polyacrylamide gel as a support with a ratio of synthetic polymer to enzyme generally greater than ten.

The method according to the present invention, permits to achieve immobilization of a very high quantity of enzymes, preferably in superficial zones or in zones easily accessible of the matrix which acts as the solid support and which consists of polysaccharides utilizing small quantities of vinyl monomers, the quantities of the vinyl monomers frequently being less than or equal to the quantity of the enzyme. The method according to the present invention also permits to eliminate all pre-reactions with substances, as it is frequently the case with vinyl-enzymes which lead to non-homogenous products with respect to the degree of substitution and which are also responsible for phenomena of deactivation of the enzymes. It is also possible with the method according to the present invention, to avoid all the drawbacks which are found in the case of copolymerization reactions initiated by high energy radiation, which reactions lead frequently to a deactivation of the enzymes and/or to products having kinetic properties sufficiently different from the properties of the free enzymes used as the starting material. In particular, several enzymes immobilized on copolymers have been prepared in the past after vinylation of the enzyme molecule on matrices of a polycarbohydrate but the efficiency of the reaction is not satisfactory.

It has now been found that by the proper selection of the system used to start the polymerization reaction, proper selection of the matrix used as a support and proper selection of the vinyl monomer and the enzyme, it is possible to obtain enzymes immobilized on a pre-formed solid matrix insoluble in an aqueous phase so that the matrix retains in an appreciable manner the original biological activity of the enzyme.

More specifically, it is possible to obtain products with increased efficiency of immobilization of the enzyme, with kinetic properties more similar to the properties of the free enzyme utilizing a substantially less complex technology. The products are obtained in the form of powders, fibers, beads, films, sheets, gels, depending on the nature of the matrix used as the support.

The crux of the present invention resides in the formation of free radicals generated by ultra-violet light in the presence of suitable metallic chlorides which transfer easily their activity to both the matrix used as the support as well as to the enzyme and to the vinyl monomer according to the following reaction scheme:

$MeX_n + h\nu + support = support.$
$MeX_n + h\nu + enzyme = enzyme.$
$MeX_n + h\nu + monomer = monomer.$
$X = Cl: n = 2, 3$ or $4$; $Me = Fe$;

The chlorides of cerium and copper as well as other metals may also be used but the chloride of iron is preferable. The formation of the enzyme immobilized on the copolymer proceeds through a polymerization of the monomer and ends in accordance with the usual possible reactions of termination of macroradicals during the stage of growth of the polymer, that is principally by transfer to monomer molecules, transfer to macromolecules of enzyme, transfer to macromolecules of the support or combination of two macroradicals.

According to the process of the present invention, a suspension or solution of a polycarbohydrate in an aqueous medium may be used. The vinyl monomer and the enzyme, preferably in an aqueous solution, are simultaneously added followed by the catalyst which generally consists of a ferric salt. Thereafter, oxygen dissolved in the suspension or solution is eliminated by bubbling nitrogen or another inert gas through. Thereafter, a source of ultraviolet light having a spectrum between about 250 and about 340 mμ used to irradiate the material. The radiation is allowed to proceed for a period of time between a few minutes and about one hour. The solid material thus obtained after thorough washing, may be used as such or may be preserved in the damp state or may be lyophilized.

It has been found that particularly suitable are vinyl monomers of formula

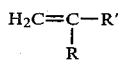

in which R is hydrogen or methyl, R' is CN or COOR" in which R" is a lower alkyl, the latter optionally containing epoxy or hydroxy groups. It has also been found that some N-acryloyl derivatives of nitrogenous heterocyclic compounds may be also equally suitable, such as for instance, N,N'-bis-acryloylpiperazine and N,N,N"-tris-acryloyl-symmetrical hexahydrotriazine.

It should be noted that the ferric salt in the concentrations conventionally used, acts in many cases as inhibitor of the enzymatic reaction, while in the process according to the present invention, the inhibitory effect attributable to the iron is substantially reduced or even zero.

It has been found that the formation of an enzyme immobilized on the copolymer is achieved during the process according to the present invention. This formation is demonstrated by the following experiment which additionally shows the possibility of immobilizing every type of protein, that is proteins which may not necessarily have enzymatic activity.

Immobilization of Albumen with Methylacrylate

Albumin in the amount of 100 mgs is dissolved in five ml. of water. A portion of 250 mls. of methylacrylate is added and the material is exposed to ultraviolet radiation from a lamp, at a low pressure of mercury vapor such as the Philips lamp in the presence of ferric chloride, $FeCl_3$, in an amount between 0.1 and 100 mM. Nitrogen is bubbled through the solution to remove oxygen gas. The reaction is allowed to proceed for a period of thirty minutes. The product thus formed precipitates from the milky solution by the addition of one volume of methanol at a temperature of between 4° and 20° C. The precipitate is recovered and extracted repeatedly with acetone, which is a solvent for the polymethylacrylate but is not a solvent for the albumin, at a temperature between 4° and 10° C. for the purpose of removing the homopolymer, that is the polymethacrylate which may have been formed.

The residue insoluble in acetone is repeatedly extracted with a buffer of pH 5.6 which is a solvent for the albumin, for the purpose of removing any amount of unreacted albumin which may be present. The extraction procedure with acetone and with the aqueous solution is repeated with the residue. In this manner, there is obtained as the final product, a residue insoluble in acetone and in water which is subject to infrared analysis. The spectrum shows absorption bands which are attributable to both the albumin and the polymethacrylate so that the composition of the copolymer is confirmed.

In accordance with the process of the present invention, it is possible to prepare in general, copolymers of any enzyme and in particular, proteolytic enzymes such as papain, trypsin, and chymotrypsin.

The process is also applicable to hydrolytic enzymes such as amylases, cellulases, β-glucuronidase-arylsulfatases, esterases, heparinases, penicillinamidases, and ureases; oxidases such as aminoacidoxidases, diaphorases, glucoseoxidases and peroxidases; hydrogenases such as steroidodehydrogenases, lactic acid dehydrogenases, alcohol-dehydrogenases; catalases; isomerases such as invertases and steroidoisomerases.

As it has been mentioned already hereinabove it is possible to prepare copolymers of polysaccharides and proteins, also in the case in which the proteins are not enzymes.

Several examples hereinbelow illustrate the present invention with several monomers, several enzymes, and several supports.

EXAMPLE 1

Preparation of cellulose-copolyglycidylmethylacrylate-peroxidase

Cellulose in the amount of 100 milligrams in a variety of physical forms such as fibers, films, or sheets is suspended in 10 ml of water. There is then added $FeCl_3$ in an amount between 0.1 and 100 mg while the pH is adjusted to a value of about 4. Peroxidase, for instance, the type called "Horseradish peroxidase" is added in the amount of 1–100 mg and also 1–100 mg of glycidylmethacrylate. The mixture is irradiated with a source of ultraviolet light at a low pressure of mercury vapor, while provision is made to absorb the thermic radiations with a suitable filter. The copolymerization is allowed to proceed in a nitrogen atmosphere for a period of 30 minutes.

The solid material which is obtained, is repeatedly washed with a buffer solution of pH 6 and then repeatedly with a 0.3% M NaCl solution. Finally, the enzymatic activity of the copolymer is determined carrying out the specific reaction for the peroxidase, for instance, a spectrophotometric determination with $H_2O_2$-guaiacol or p-aminophenazone. There is obtained a reaction efficiency expressed in terms of the amount of enzymatic activity which is immobilized per amount of enzymatic activity which is reacted, multiplied by 100, between 10 and 24% depending on the concentration of the enzyme.

The copolymer which may be preserved also in the moist state at a temperature between 4° and 5° C. retains 80% of its activity after more than one year. The analytical properties correspond to the properties of the composition containing cellulosepolyglycidylmethacrylate-peroxidase.

EXAMPLE 2

Preparation of cellulose-copolymethacrylateperoxidase

The reaction as in example 1 is repeated with the difference that the vinyl monomer is methylacrylate. The solid material recovered from the reaction is washed with solutions of pH 5.3. On the basis of the determination of the enzymatic activity of the copolymer, the efficiency of immobilization corresponds to a value of 3%.

EXAMPLE 3

Preparation of cellulose-copolyacrylonitrileperoxidase

The reaction described in example 1 is repeated with the following modifications:

the cellulose is 5 grams of swollen material in the form of beads, the vinyl monomer is acrylonitrile and the copolymer, after washing with solutions of pH 5.3, exhibits peroxidase activity and the efficiency of the reaction is 70%.

EXAMPLE 4

Preparation of cellulose-copolymethylmethacrylateperoxidase

The reaction as described in example 2 is repeated with the modification that the vinyl monomer is methylmethacrylate. The efficiency of the reaction is 7%.

EXAMPLE 5

Preparation of cellulose-copoly(hexahydro-trisacryloyl-s-triazine)

The reaction as described in example 1 is repeated with the modification that the monomer is hexahydro-triacryloyl-s-triazine. The efficiency of the reaction is 28%.

EXAMPLE 6

Preparation of cellulose-copoly(bis-acryloylpiperazine)

The reaction as described in example 1 is repeated with the modification that the vinyl monomer is bis-acryloylpiperazine. The efficiency of the reaction is 20%.

EXAMPLE 7

Preparation of Sepharose ®-copolyglycidylmethacrylate-cellulase

Sepharose ® in the amount of 100 mg is suspended in 10 ml of water. There is added 0.1–100 mg of $FeCl_3$ and the pH is adjusted to between 4 and 5.1 per 100 mg of cellulase such as Cellulase F and glycidylmethacrylate in the amount of between 1 and 100 mgs. One of the monomers used in examples 2–6 may also be used. The temperature is kept lower than 20° C. Irradiation is carried out with a source of ultra violet light with mercury vapor at low pressure. The copolymerization is allowed to proceed for thirty minutes. The copolymer is washed as in example 1 and the enzymatic activity is determined with a carboxymethylcellulose as a substrate. The efficiency of immobilization which is calculated on the basis of the activity measurement is 82%.

EXAMPLE 8

Preparation of Sepharose ®-copolyglycidylmethacrylate-α-amylase

α-amylase is immobilized with the identical reaction reported in example 7 with the only modification that the enzyme is α-amylase. The efficiency of immobilization is

EXAMPLE 9

Preparation of Sepharose ®-copoly(hexahydrotriacryloyl-s-triazine)-peroxidase

The reaction of immobilization is repeated with Sepharose ® as described in example 7, with the following modifications:

The enzyme being used is peroxidase and the vinyl monomer is hexahydro-triacryloyl-s-triazine. The immobilization efficiency is 38%.

EXAMPLE 10

Preparation of Sepharose ®-copolyglycidylmethacrylate-glucose-oxidase

The reaction described in example 6 is repeated with the modification that the enzyme being used is glucoseoxidase(E.C.). The immobilization efficiency is 52%.

EXAMPLE 11

Preparation of Starch-copolyglycidylmethacrylate-peroxidase

Starch, in the amount of 100 mgs is dissolved in 10 ml of water. Additions are made: $FeCl_3$ in the amount of 0.1–100 mgs while adjusting the pH to 4; glycidylmethacrylateperoxidase in the amount of 1–100 mgs is added. One of the monomers used in examples 2–7 may also be used. The temperature is kept lower than 20° C. Then a source of ultraviolet light, that is a low pressure mercury vapor lamp is used. The copolymerization is allowed to proceed for thirty minutes. The precipitate which is obtained is washed as in example 1 and the activity of the copolymer is determined. The efficiency of immobilization calculated on the basis of the activity measurement is 40%.

The analytical properties of the product correspond, as expected, to a product containing starchpolyglycidylmethacrylate-peroxidase.

The examples described in detail hereinabove are only some of the examples which illustrate the method of immobilization of enzymes on a solid support consisting of a polycarbohydrate by means of simple reactions of immobilization. Obviously, the efficiency of the process depends upon a number of factors, such as the physical properties of the support, the physical properties of the monomer and the physical properties of the enzyme.

It should also be noted that it is possible to immobilize on the same matrix several enzymes simultaneously.

What is claimed is:

1. A process for the preparation of a copolymer of a polysaccharide having enzymatic activity, which comprises adding to a suspension of a polysaccharide in an aqueous medium, a vinyl monomer and an enzyme, wherein the vinyl monomer is an N-acrloyl derivative of a nitrogenous heterocyclic compound or a monomer of the formula

in which R is hydrogen or methyl, R' is CN or COOR", and R" is lower alkyl, epoxy substituted lower alkyl or hydroxy substituted lower alkyl, then adding a catalyst which comprises a ferric salt and irradiating the resulting mixture with ultraviolet light to cause polymerization and form said copolymer.

2. The process according to claim 1 wherein in said vinyl monomer R'' is epoxy substituted lower alkyl or hydroxy substituted lower alkyl.

3. The process according to claim 1 wherein said vinyl monomer is methylacrylate.

4. The process according to claim 1 wherein the vinyl monomer is glycidylmethacrylate.

5. The process according to claim 1 wherein the vinyl monomer is acrylonitrile.

6. The process according to claim 1 wherein said vinyl monomer is a N-acryloyl derivative of a compound containing a nitrogenous heterocyclic ring.

7. The process according to claim 6 wherein the vinyl monomer is bis-acryloylpiperazine.

8. The process according to claim 6 wherein the vinyl monomer is symmetrical N,N',N''-trisacryloyl-hexahydrotriazine.

9. The process according to claim 1 wherein the enzyme is a proteolytic enzyme selected from the group consisting of papain, trypsin and chymotrypsin.

10. The process according to claim 1 wherein the enzyme is a hydrolytic enzyme which is a member selected from the group consisting of amylases, cellulases, β-glucuronidase-arylsulfatases, esterases, heparinases, penicillinamydases and ureases.

11. The process according to claim 1 wherein the enzyme is an oxidase which is a member selected from the group consisting of aminoacidoxidases, diaphorases, glucoseoxidases and peroxidases.

12. The process according to claim 1 wherein the enzyme is a dehydrogenase selected from the group consisting of steroidodehydrogenase lactic acid hydrogenase and alcohol-dehydrogenase.

13. The process according to claim 1 wherein the enzyme is a catalase.

14. The process according to claim 1 wherein the enzyme is an isomerase which is a member selected from the group consisting of invertases and steroidoisomerases.

* * * * *